(12) United States Patent
Adam et al.

(10) Patent No.: US 9,918,466 B2
(45) Date of Patent: Mar. 20, 2018

(54) ANTIMICROBIAL POLYMERS AND METHODS FOR THEIR PRODUCTION

(71) Applicant: EMPIRE TECHNOLOGY DEVELOPMENT LLC, Wilmington, DE (US)

(72) Inventors: Georgius Abidal Adam, Edensor Park (AU); Scott Andrew Needham, Mangerton (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/760,740

(22) PCT Filed: Jan. 14, 2013

(86) PCT No.: PCT/US2013/021383
§ 371 (c)(1),
(2) Date: Jul. 14, 2015

(87) PCT Pub. No.: WO2014/109765
PCT Pub. Date: Jul. 17, 2014

(65) Prior Publication Data
US 2015/0366188 A1    Dec. 24, 2015

(51) Int. Cl.
| | | |
|---|---|---|
| *C09D 5/14* | (2006.01) | |
| *A01N 25/24* | (2006.01) | |
| *C08F 291/00* | (2006.01) | |
| *C08K 5/31* | (2006.01) | |
| *C08J 3/22* | (2006.01) | |

(52) U.S. Cl.
CPC ............ *A01N 25/24* (2013.01); *C08F 291/00* (2013.01); *C08J 3/226* (2013.01); *C08K 5/31* (2013.01); *C09D 5/14* (2013.01); *C08J 2323/06* (2013.01); *C08J 2323/12* (2013.01); *C08J 2327/06* (2013.01); *C08J 2329/04* (2013.01); *C08J 2423/06* (2013.01); *C08J 2427/06* (2013.01); *C08J 2429/04* (2013.01); *C08J 2469/00* (2013.01)

(58) Field of Classification Search
CPC ................ C08J 3/226; C08K 5/31; C09D 5/14
USPC .................................................. 523/122, 351
See application file for complete search history.

(56) References Cited

U.S. PATENT DOCUMENTS

| | | |
|---|---|---|
| 7,250,453 B2 | 7/2007 | Sakuma et al. |
| 7,705,073 B2 | 4/2010 | Pudleiner et al. |
| 2002/0064652 A1 | 5/2002 | Lau et al. |
| 2005/0170193 A1 | 8/2005 | Kelley et al. |
| 2006/0134163 A1 | 6/2006 | Bagwell et al. |
| 2006/0217515 A1 | 9/2006 | Getman et al. |
| 2008/0193496 A1 | 8/2008 | Gabbay |
| 2011/0233810 A1 | 9/2011 | Neigel et al. |

FOREIGN PATENT DOCUMENTS

WO        2011129982 A2    10/2011

OTHER PUBLICATIONS

Antimicrobial Polymer, http://en.wikipedia.org/wiki/Antimicrobial_polymer, Jul. 9, 2012.
Getman, Gerry D., Advanced Non-Toxic Polymeric Antimicrobial for Consumer Products, http://digital.ipcprintservices.com/display_article.php?id=752246, Jul. 9, 2012.
High-performance antimicrobial masterbatch, HeiQ AGS-20 MGB, Swiss Innovation Technology, provided by HeiQ Materials AG, Switzerland, www.heiqmaterials.com (no date available).
McCubbin et al., Covalent Attachment of Quaternary Ammonium Compounds to a Polyethylene Surface via a Hydrolyzable Ester Linkage: Basis for a Controlled-Release System of Antiseptics from an Inert Surface, Journal of Applied Polymer Science (2006) 100:538-545.
Punyani, Supriya et al., "Preparation of Iodine Containing Quaternary Amine Methacrylate Copolymers and Their Contact Killing Antimicrobial Properties," Journal of Applied Polymer Science (2006), 102:1038-1044.
Schulman, Polybatch Abact Antibacterial and AMIC Antimicrobial Masterbatches, pp. 1-2 (no date available).
Ye et al., Solventless hybrid grafting of antimicrobial polymers for self-sterilizing surfaces, Journal of Materials Chemistry (2011), 21:13188-13194.

*Primary Examiner* — Edward Cain
(74) *Attorney, Agent, or Firm* — Pepper Hamilton LLP

(57) ABSTRACT

Antimicrobial or antiseptic polymers may be produced by incorporation of an antimicrobial ingredient into the polymer by grafting, copolymerization, or via a combined antimicrobial/plasticizer ingredient. The polymer may be produced as a masterbatch, or a ready to process polymer for producing antimicrobial products. The reactions may be conducted in a reactive extruder to provide a single-step synthesis.

30 Claims, 3 Drawing Sheets

FIG. 3A
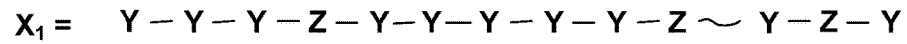
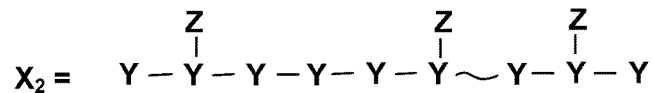
FIG. 3B
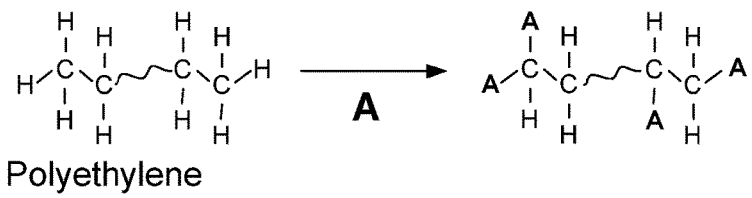
Polyethylene
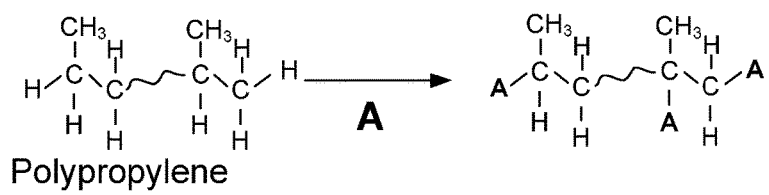
Polypropylene
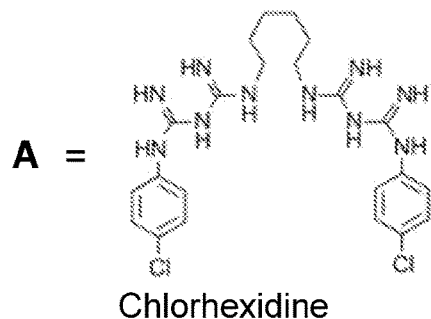
Chlorhexidine
FIG. 4 bisphenol A    phosgene    Polycarbonate

ANTIMICROBIAL POLYMERS AND METHODS FOR THEIR PRODUCTION

CLAIM OF PRIORITY

This application is a U.S. national stage filing under 35 U.S.C. § 371 of International Application No. PCT/US2013/021383 filed on Jan. 14, 2013 entitled "ANTIMICROBIAL POLYMERS AND METHODS FOR THEIR PRODUCTION," which is incorporated herein by reference in its entirety.

BACKGROUND

Polymers used in the packaging of food materials, medical equipment, and children's novelty toys are subjected to contamination with bacteria and other microbial species. Sterilized or antiseptic products or packaging materials are required for any item that is in contact with food or human contact as well as certain medical diagnostic procedures. Antimicrobials or antiseptics are chemical compounds that reduce or mitigate the growth or development of microbial organisms, may be incorporated into products for reducing contamination by bacteria or other microbes. This may be achieved by a variety of mechanisms dependent upon the mode of action, composition, degree of activity, and application. The use of the antimicrobial compounds leads to either death or arrested growth of the targeted microorganisms. Since their discovery in the early 1900s, antimicrobial agents have transformed the prevention and treatment of infectious diseases. They are currently employed across a very broad spectrum of applications.

Antimicrobials, however, in greater concentrations can also be potentially hazardous to human health and to the environment. Antimicrobials have been determined to be the cause of skin irritations, and have been linked to increased susceptibility to allergies. Antimicrobials may also be washed into our water streams, and some antimicrobials, such as triclosan, for example, are toxic to aquatic organisms, particularly algae, and have been found to accumulate in fish. Therefore, it is desirable to have non-leaching antimicrobial materials that remain effective over the life of usage and that reduce the risk of creating adaptable resistant microorganisms. Depending on the methods used to incorporate the antimicrobial agents into a product, such as a polymer, almost all treatments fall into one of the following three categories: 1) adsorption of the antimicrobial agent to the surface of materials ether passively or in combination with surfactants or surface-bonded polymers; 2) incorporation of the agent into a polymer coating applied on the material surface; or 3) compounding the agent into the bulk material comprising the device. Among these, perhaps the most common strategy involves the impregnation of antimicrobial agents into a polymer binder applied to the device surface.

Providing ubiquitous packaging materials with antimicrobial and antiseptic properties, or producing new antiseptic polymers for such applications have a large and immediate global market. Several types of antimicrobial polymers are used to some extent, but they remain expensive due to the need to prepare specialized active monomers or the need to subsequently coat the finished article with the antiseptic materials. This additional processing step is not trivial from a processing and coating stability perspective. Therefore, there remains a need for cost effective methods of mass production of antimicrobial polymers.

SUMMARY

Cost effective methods of mass production of antimicrobial polymers may be achieved by using the processing technologies of either masterbatching and/or reactive extruder technology. Antimicrobial polymers may also be produced using antiseptic active molecules during polymer production to act as polymer chain end termination molecules, or chain transfer agents.

In an embodiment, a method for making an antimicrobial masterbatch includes mixing an antimicrobial ingredient with a high melt flow rate polymer and a catalyst at a temperature, shear and pressure sufficient to graft the antimicrobial ingredient to the polymer to form the antimicrobial masterbatch.

In an embodiment, a method for making an antimicrobial polymer includes mixing a polymer with a dual acting ingredient having both plasticizer and antimicrobial properties at a temperature, shear and pressure sufficient to distribute the dual acting ingredient into the polymer to form the antimicrobial polymer.

In an embodiment, a method for producing an antimicrobial polymer includes copolymerizing a reaction mixture comprising a first polymerizable co-monomer having antimicrobial properties; and a second polymerizable co-monomer.

In another embodiment, a method for producing antimicrobial polymer products includes charging a reactive extruder with a high melt flow rate polymer, a catalyst and an antimicrobial ingredient, operating the reactive extruder at a temperature, shear and pressure sufficient to graft the antimicrobial ingredient to the high melt flow rate polymer to form an antimicrobial masterbatch, and extruding the antimicrobial masterbatch. Antimicrobial polymer products may then be produced by mixing the antimicrobial masterbatch with a melt-processable polymer, applying heat, shear and pressure to the mixture to disperse the antimicrobial ingredient of the antimicrobial masterbatch into the melt-processable polymer to produce an antimicrobial polymer, and processing the antimicrobial polymer into antimicrobial polymer products capable of inhibiting growth of microorganisms in or on the antimicrobial polymer products.

In a further embodiment, a method for producing an antimicrobial polymer includes mixing a high melt flow rate polymer and an antimicrobial ingredient to produce a reactive mixture, and subjecting the reactive mixture to a temperature, pressure and shear sufficient to covalently bond the antimicrobial ingredient to the polymer at at least one of: ends of the high melt flow rate polymer and a backbone of the high melt flow rate polymer to produce an antimicrobial polymer that is suitable for production of final products.

BRIEF DESCRIPTION OF THE FIGURES

FIGS. 3A and 3B show representations of polymers with copolymerized and grafted moieties according to embodiments.

FIG. 4 shows examples of polymers converted to antimicrobial polymers by direct grafting according to an embodiment.

DETAILED DESCRIPTION

Polymers with antimicrobial properties, and methods for producing the polymers are disclosed herein. To provide polymers with antimicrobial effectiveness, one or more antimicrobial ingredients may be covalently bonded with the polymers. In an embodiment, one or more antimicrobial ingredients may be grafted to polymers in a masterbatch process. Some examples of antimicrobial ingredients that may be bonded include, but are not limited to quaternary ammonium salts, quaternary phosphonium salts, chlorhexidine derivatives, polyhexamethylene biguanide derivatives, povidone iodine, starch-iodine derivatives, and combinations thereof.

In an embodiment, some examples of polymers that may be modified with antimicrobial components include, but are not limited to polyolefins. In an alternative embodiment, the polymer may be, but is not limited to any of the following: polyethylene, polypropylene, polymethylpentene, poly-butene-1, ethylene-vinyl acetate copolymer, polystyrene, polyethylene terephthalate, polyvinyl acetate, polycarbonate, polyamide, polyvinyl alcohol, polyvinylidene chloride; acrylonitrile butadiene styrene copolymers, acrylic polymers, acrylamide polymers, acrylate polymers, polysulfones, vinyl chloride polymers, butyl rubber, isoprene rubber, silicone thermoplastics, copolymers thereof, and any compatible combinations thereof.

In an alternative embodiment, the polymer may be a polymer having a high melt flow rate. The polymer may have a melt flow index of about 10 g/10 minutes to about 50 g/10 minutes, as measured in accordance with ASTM D-1238 at 190° C. and 2.16 kg load. As specific examples, the polymer may have a melt flow index of about 10 g/10 minutes, about 15 g/10 minutes, about 20 g/10 minutes, about 25 g/10 minutes, about 30 g/10 minutes, about 35 g/10 minutes, about 40 g/10 minutes, about 45 g/10 minutes, or about 50 g/10 minutes, or an value between any of the listed values or greater than or less than any of the listed values. Melt flow index is a measure of the ease of flow of the melt of a thermoplastic polymer. Melt flow index is defined as the mass of polymer, in grams, flowing in ten minutes through a capillary of a specific diameter and length by a pressure applied via prescribed alternative gravimetric weights for alternative prescribed temperatures. The method is described in the ASTM D-1238 and ISO 1133 standards. Melt flow rate is an indirect measure of molecular weight, with high melt flow rate corresponding to low molecular weight. At the same time, melt flow rate is a measure of the ability of the melt to flow under pressure. Melt flow rate is inversely proportional to viscosity of the melt at the conditions of the test (melt viscosity is also dependent on the force applied).

Figure 1:
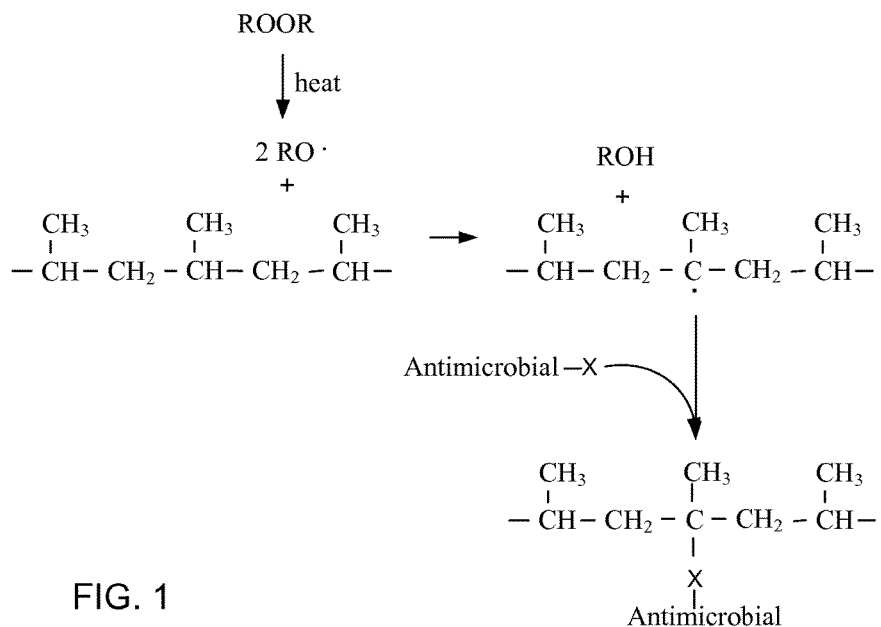
FIG. 1 depicts an illustrative method for producing an antimicrobial polymer by peroxide catalysis according to an embodiment.

Modification of polymers through the action of a catalyst in accordance with a reaction procedure as represented in FIG. 1, may be done at a temperature, shear and pressure sufficient to graft the antimicrobial ingredient to the polymer. The catalyst may be a molecule which has a peroxide group. The catalysts may also be azo-compounds or diazo-compounds. The catalyst may comprise peroxides, peroxy esters, and hydroperoxides. The reactive mixture may be heated to a temperature sufficient to decompose the peroxide into oxyl radicals, and melt the polymer to a melt processable state. The oxyl radicals may then remove a hydrogen from the polymer and/or the antimicrobial-active ingredient, producing reactive sites on the polymer to bond with reactive sites of antimicrobial molecules.

The resultant antimicrobial polymer may be configured with a concentrated amount of antimicrobial ingredient to be used as a masterbatch so that optimum loading of the masterbatch is provided. In an embodiment, an amount of the antimicrobial ingredient in a masterbatch may be from about 20 wt % to about 50 wt % of an amount of the polymer. As specific examples, the amount of antimicrobial ingredient may be about 20 wt %, about 22 wt %, about 24 wt %, about 26 wt %, about 28 wt %, about 30 wt %, about 32 wt %, about 34 wt %, about 36 wt %, about 38 wt %, about 40 wt %, about 42 wt %, about 44 wt %, about 46 wt %, about 48 wt %, about 50 wt %, or any amount between any two of the listed values, and also may include amounts that may be less than or greater than the listed values.

The peroxide is a catalyst for the reaction. In an embodiment, an amount of peroxide from about 0.025 wt % to about 0.05 wt % of an amount of the polymer may be mixed with the polymer and antimicrobial ingredient. As specific examples, the amount of peroxide may be about 0.025 wt %, about 0.0275 wt %, about 0.03 wt %, about 0.0325 wt %, about 0.035 wt %, about 0.0375 wt %, about 0.04 wt %, about 0.0425 wt %, about 0.045 wt %, about 0.0475 wt %, about 0.05 wt %, or any amount between any two of the listed values, and also may include amounts that may be less than or greater than the listed values.

In an embodiment, the peroxide may be essentially any peroxide containing molecule having a decomposition temperature which is about 10° C. to about 20° C. lower than the melt processing temperature of the polymers. This decomposition temperature may be above about 125° C. At the decomposition temperature, the peroxide may decompose into oxyl radicals (see initial step in FIG. 1). In a further embodiment, the peroxide may be, but is not limited to, one of: benzoyl peroxide; cumyl peroxide; dicumyl peroxide; cumyl hydroperoxide; t-butyl cumyl peroxide; 1,3-bis(t-butylperoxyisopropyl)benzene; t-butyl hydroperoxide; di-t-butyl peroxide; 2,5-dimethyl-2,5-di(t-butylperoxy)hexane; t-butyl-perbenzoate; 1,1,3,3-tetramethylbutyl hydroperoxide; 2,5-dimethylhexyl 2,5-diperoxy-benzoate; 2,5-dimethylhexane 2,5-dihydroperoxide; 2,5-dimethyl 2,5-bis(t-butylperoxy)hexene-3, or combinations thereof.

Figure 2:
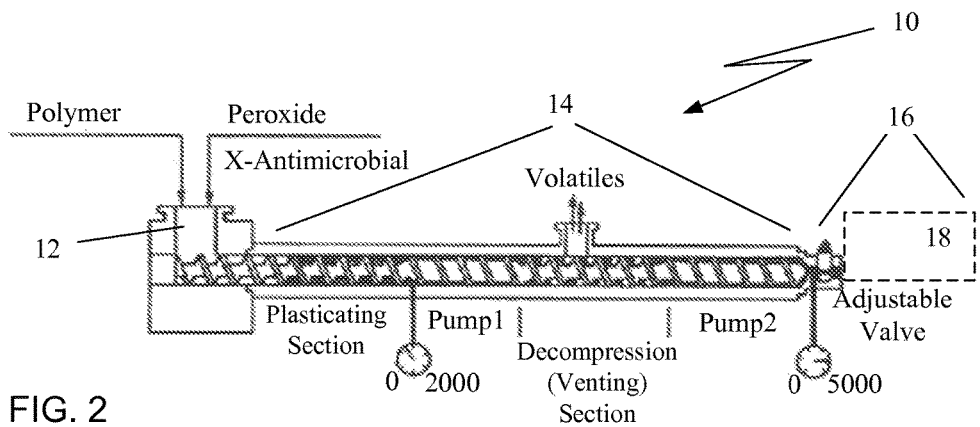
FIG. 2 depicts a reactive extruder for producing an antimicrobial according to an embodiment.

In an embodiment, an antimicrobial masterbatch may be prepared by the above-described reaction process. The antimicrobial masterbatch may be prepared in a reactive extruder 10 at a temperature, shear and pressure sufficient to graft the antimicrobial ingredient to the polymer. The required temperature and pressure may be a function of the peroxide and polymer used, and may be selected to be sufficient for decomposing the peroxide under controlled conditions and melt processing of the polymer. An example of a reactive extruder 10 may be represented by the illustration in FIG. 2. A reactive extruder 10 may include an entry port 12 for introducing the reactants, a mixing and processing section 14 for combining and reacting of the constituents, and an exit port 16 for extruding the masterbatch. In addition, the extruder 10 may also include an optional sizing device 18 to produce pills or pellets of the masterbatch of a desired size. Alternatively, the extruded masterbatch could be ground or granulated in an additional processing system.

By reactive extrusion low-cost commercially available polymers may be converted into materials with tailor-made properties of increased value in a single processing step.

Reactive extruders 10 may act essentially simultaneously as conventional polymer processing machinery and as pressure vessels for chemical synthesis in highly viscous media. Unlike in traditional organic chemistry, where the final product very often is obtained by multi-step synthesis, reactive extrusion provides high-yield, one-step synthesis with very short reaction times. Volatile by-products may be removed in the venting section, and additional uneconomical purification and separation processes may not be necessary.

In an alternative embodiment, as depicted in FIG. 3A, an antimicrobial ingredient may be directly, and randomly copolymerized into a polymer such as is represented by $X_1$, as compared with antimicrobial ingredient grafted directly onto the polymer chain such as is represented by $X_2$ and discussed previously. For the copolymer $X_1$, a monomeric species Y may be a condensation monomer having at least two polymerizable groups per molecule, and an antimicrobial ingredient Z may be copolymerized into the polymer along with the monomers Y. Monomers Y may be at least one member selected from the group comprising: an olefenic co-monomer, a condensation co-monomer, and a cyclic monomer. In further embodiments, the monomers Y may be at least one member selected from the group comprising: ethylene, propylene, vinylacetate, acrylate, diols, diamines, diacids, diesters, diisocyanates, diepoxides, caprolactam, and caprolactone, and may include terephthalic acid, phthalic acid, adipic acid, ethylene glycol, butanediol, hexamethylenediamine, or additional olefinic co-monomer for addition polymerization. Some examples of polymerizable antimicrobial ingredients may include clorhexidene-7-octenoate, chlorhexidine-3-butenoate, chlorhexidine-5-hexenoate, as reactive condensation co-monomers, or 1-heptadecenyltrimethylammonium bromide, or any unsaturated quaternary ammonium salt derivatives for addition co-monomers.

Another ingredient that is commonly used in polymer production is a plasticizer. A plasticizer may be any of various substances having the required technical specifications, that when added to polymers or other materials, makes the material easier to process and makes or keeps the material soft or pliable. Plasticizers work by embedding themselves between chains of polymers, spacing the chains apart (increasing the "free volume"), and thus significantly lowering the glass transition temperature for the material, making the material softer. In an embodiment, instead of providing and adding separate antimicrobial ingredient and plasticizer, at least one dual acting antimicrobial-plasticizer ingredient may be configured and introduced as a single component along with the peroxide and the polymer. A polymer having a dual acting ingredient may have a weight ratio of the polymer to the dual acting ingredient of from about 100:1 to about 100:2. As specific examples, the weight ratio of polymer to dual acting ingredient may be about 100:1.0, about 100:1.1, about 100:1.2, about 100:1.3, about 100:1.4, about 100:1.5, about 100:1.6, about 100:1.7, about 100:1.8, about 100:1.9, about 100:2.0, or any weight ratio between any of the listed values or greater than or less than the listed values.

The dual acting antimicrobial-plasticizer ingredient may have the antimicrobial ingredient covalently bonded with the plasticizer (AP in FIG. 3B). The antimicrobial ingredient may be covalently bonded with the plasticizer and mixed into a melt-processable polymer. The mixing may be conducted in an extruder, such as a reactive extruder 10, in a manner as discussed above. Some examples of plasticizers to which the antimicrobial ingredient may be covalently bonded include, but are not limited to ester class plasticizers such as: butyl adipate, butyl sebacate, isooctyl caproate, aliphatic diesters, low molecular weight aliphatic polyesters, or low molecular weight polyethers, low molecular weight polyamides, and any combinations thereof. Some examples of dual plasticizer-antimicrobial ingredients may include, but are not limited to, chlorhexidine butyrate, chlorhexidine octanoate, chlorhexidine caproate, chlorhexidine digluconate, biguanide grafted to low molecular weight polymeric plasticizers, cetyltrimethylammonium bromide grafted to low molecular weight polymeric plasticizers.

A masterbatch may similarly be produced with the dual acting plasticizer-antimicrobial ingredient. The masterbatch may be configured so that the weight ratio of the high melt flow rate polymers to the dual acting plasticizer-antimicrobial ingredient in the masterbatch is from about 1:20 to about 1:50. As specific examples, the weight ratio of polymer to dual acting ingredient in a masterbatch may be about 1:20, about 1:22, about 1:24, about 1:26, about 1:28, about 1:30, about 1:32, about 1:34, about 1:36, about 1:38, about 1:40, about 1:42, about 1:44, about 1:46, about 1:48, and about 1:50, or any weight ratio between any of the listed values or greater than or less than the listed values.

Any of the antimicrobial masterbatches produced as discussed above may be used for producing a polymer product capable of inhibiting growth of microorganisms in or on the polymer product. A masterbatch containing a concentrated antimicrobial ingredient may be mixed with additional melt processable polymer to provide a polymer mix. The additional melt processable polymer may be the same as, or at least compatible with, the polymer of the masterbatch so that a uniform distribution in the final processed polymer may occur. Non-compatible polymers may result in phase separation occurring while processing of the polymer and forming final products. The melt processable polymer may be any of the polymers presented above. An amount of heat, shear and pressure sufficient for melt processing of the masterbatch and the melt processable polymer in the mixture may be applied to the mixture to disperse the antimicrobial ingredient of the masterbatch into the melt-processable polymer to produce an antimicrobial polymer. The antimicrobial polymer may be processed into products having antimicrobial properties. Some examples of products may include food packaging, medical instruments, diagnostic tools, and toys.

The antimicrobial polymer may be processed by any of a variety of processing techniques to produce finished products. Some examples of processing techniques may include, but are not limited to vacuum forming, blow molding, injection molding, extrusion, reactive extrusion, rotational molding, injection blow molding, compression molding, solution casting, emulsion and spraying.

A desired amount of antimicrobial ingredient in the polymer product may be from about 0.25 wt % to about 2 wt % of the amount of the melt processable polymer in the polymer product, and may as specific examples be about 0.25 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, any value between any of the listed values, or an amount which may be greater than or less than the listed values. As provided above, an amount of antimicrobial ingredient in the antimicrobial masterbatch may be about 20 wt % to about 50 wt % of an amount of the polymer carrier.

A ratio of the masterbatch to the melt-processable polymer in the mixture may therefore range from about 1:80 (using masterbatch with about 20 wt % antimicrobial ingredient to produce polymer product with about 0.25 wt % antimicrobial ingredient) to about 1:50 (using masterbatch with about 50 wt % antimicrobial ingredient to produce polymer product with about 1 wt % antimicrobial ingredient). The ratio may ultimately depend on the desired amount of antimicrobial ingredient in the product and the amount of antimicrobial ingredient in the concentrated masterbatch.

In additional embodiments, existing polymers may be modified to be antimicrobial polymers by bonding an antimicrobial ingredient directly to the polymer, as shown by X2 in FIG. 3A. The existing polymers may be standard commercial polymers, and may include, but are not limited to any of the following: polyethylene, polypropylene, polymethylpentene, polybutene-1, ethylene-vinyl acetate copolymer, polystyrene, polyethylene terephthalate, polyvinyl acetate, polycarbonate, polyamide, polyvinyl alcohol, polyvinylidene chloride; acrylonitrile butadiene styrene copolymers, acrylic polymers, acrylamide polymers, acrylate polymers, polysulfones, vinyl chloride polymers, butyl rubber, isoprene rubber, silicone thermoplastics, copolymers thereof, and any compatible combinations thereof. The polymer may be mixed with an antimicrobial ingredient and peroxide catalyst to produce a reactive mixture, and the reactive mixture may be subjected to a temperature, pressure and shear sufficient to covalently bond the antimicrobial ingredient to the polymer at at least one of: ends of the polymer and a backbone of the polymer to produce an antimicrobial polymer. This antimicrobial polymer may be used for producing final products. In one embodiment, the reaction may be conducted in the presence of a catalyst, wherein the catalyst may be added to the reactive mixture. The catalyst may be a compound which contains a peroxide, and the peroxide catalyst, polymer and antimicrobial ingredient may be any of the previously discussed peroxides, polymers and antimicrobial ingredients.

FIG. 4 depicts examples of the polymers polyethylene and polypropylene being modified with chlorhexidine at positions along the backbone and at ends of the polymers. In an embodiment, the reaction mechanism may be essentially the same as that discussed previously with respect to the masterbatch and illustrated in FIG. 1, with the exception being the amount of antimicrobial ingredient mixed into the reactive mixture. Since a masterbatch is not being used to provide the antimicrobial ingredient, the ratio of the amount of the antimicrobial ingredient to the amount of the polymer introduced into the mix will be from about 1:100 to about 1:200, and may be, for example, about 1:100, about 1:110, about 1:120, about 1:130, about 1:140, about 1:150, about 1:160, about 1:170, about 1:180, about 1:190, about 1:200, any value between any of the listed values, or greater than or less than the listed values. The catalyst in the reactive mixture may be a peroxide and the reactive mixture may be heated to a temperature sufficient to decompose the peroxide into oxyl radicals and also to melt the polymer to a melt processable state. The oxyl radicals may then abstract a hydrogen from the polymer producing reactive sites on the polymer that may then bond with reactive sites of antimicrobial molecules.

This type of bonding of antimicrobials to polymers may also be conducted in a reactive extruder 10 wherein the polymer, the peroxide and the antimicrobial ingredient are added directly into the reactive extruder via the entry port 12. The extruder 10 may be operated at the temperature, pressure and mixing rate sufficient to graft the antimicrobial ingredient to the polymer, so that the peroxide decomposes and the polymer becomes sufficiently fluid to permit reaction with the peroxide and the antimicrobial ingredient. Once mixed, the melt may be processed to form final objects by any of the methods as previously described.

In another embodiment, the antimicrobial ingredient may be bonded to a polymer chain as a chain end terminating molecule in a condensation polymerization reaction. Some examples of condensation polymers include, but are not limited to, polyester, polycarbonate, polyamide, polyurethane, silicone polymer, polyether, polysulfone, polysulfide, hydroxyl terminated rubbers, epoxy terminated polymers and copolymers, and poly blends.

Figure 5A:
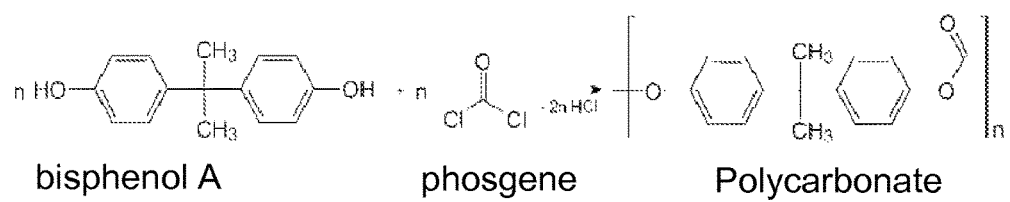
FIGS. 5A and 5B depict a polycondensation reaction with chain end modification by an antiseptic ingredient.

FIG. 5 represents the condensation formation of polycarbonate from bisphenol A and phosgene. Alternatively, diphenyl carbonate may be used in place of the phosgene. In condensation polymers, the repeating unit may be a combined moiety of at least two monomeric species with each end of the moiety having an active terminal function group that allows for condensation reactions to occur at either end. Thus, individual monomeric units may link to form a dimer, trimer, oligomer, etc., and the formed chains may condense with each other to form longer chains, until the reaction is terminated by chain end mono-functional molecules. Some examples of functional groups include, but are not limited to —OH, —COOH, —NH$_2$, —CHO, —COCl, —OR, -epoxide, —NCO, glycidyl ether, glycidyl amine, and halogens.

Figure 5B:

The terminal functional groups of the moiety may remain active during polymerization proceedings forming longer and longer chains of the repeating units (represented by the line in FIG. 5B) until blocked by a terminating group. An antimicrobial ingredient, such as chlorhexidine A (see FIG. 4), or 1-hydroxycetyltrimethylammonium bromide, as another example, may act as the terminating group, as represented in FIG. 5B, and covalently bond to the functional group at the ends of the polymer chain, thereby terminating growth of the polymer. Some antimicrobial molecules that may bond as chain terminating agents include, but are not limited to functionalized quaternary ammonium salts, quaternary phosphonium salts, chlorhexidine derivatives, polyhexamethylene biguanide derivatives, povidone iodine, starch-iodine derivatives, and combinations thereof.

An antimicrobial condensation polymer may be produced by placing at least the precursor molecules (suitable for condensation polymerization) into a reaction vessel. Reaction conditions may be provided to start the condensation and allow the molecules and chains to link together and grow, via the functional end groups, for a predetermined period of time. The length of time for the reaction will be related to the average chain length desired, with longer chains being continually formed as long as the reaction is proceeding. At the end of the predetermined period of time, an antimicrobial ingredient may be added to the reaction vessel, wherein the antimicrobial units in the antimicrobial ingredient will bond to the functional groups at the chain ends, ending the polymerization reaction and providing antimicrobial polymers.

EXAMPLES

Example 1: Production of an Antimicrobial Masterbatch

A masterbatch of polyethylene that includes about 25 wt % of the antimicrobial ingredient chlorhexidine may be produced in a screw reactive extruder 10. Individual feeds of about 1.5 kg of high melt flow rate (20 g/10 min) low density polyethylene beads, 0.505 kg (10 Mol) chlorhexidine, and 1 g of dicumyl peroxide are introduced into the entry port 12 of a laboratory scale extruder, and adjusted so that the ratio of amounts of each in wt % are about 100:33:0.05, respectively. The extruder will be heated to about 180° C. to melt the polyethylene, wherein the melted polyethylene will be mixed with the peroxide and chlorhexidine. The chlorhexidine will covalently bond to the polyethylene and masterbatch pellets will be extruded through the die and pelletizer 18. The produced master batch contains about 25 wt % of chlorhexidine as determined by elemental analysis. This master batch may be used to produce commercial antiseptic polymer and antimicrobial polymer objects.

Example 2: Production of Antimicrobial Polyethylene Sheets

The polyethylene masterbatch pellets of Example 1 may be used to produce an antimicrobial polyethylene sheet having about 0.25 wt % chlorhexidine using a laboratory scale sheet extruder. About 100 g of the masterbatch of Example 1 may be mixed with 2.5 kg of medium density polyethylene so that the amount of chlorhexidine in the final polymer will be about 0.25 wt %, thereby requiring a wt % ratio of about 25:1 of polyethylene beads to antimicrobial polyethylene masterbatch. The mixture may be fed into the laboratory scale extruder, heated to about 200° C. and extruded into an antimicrobial sheet or balloon film. Alternatively, the polymer may be extruded into a balloon film. Such a sheet may be cut to sizes suitable, for example, for use in food packaging.

Example 3: Production of Antimicrobial Polyvinyl Chloride with Combined Plasticizer-Antimicrobial Ingredient About one kg of polyvinyl chloride (PVC) resin may be mixed with about 500 g of chlorhexidine isoactanoate (about 50 wt %) and extruded into pellets of PVC. The product contains a net amount of about 45 wt % of antimicrobial chlorhexidine. The master batch PVC may be mixed with about 100 times by weight of commercial PVC and extruded to produce a sheet of antimicrobial PVC which contains about 0.34 wt % of chlorhexidine.

Example 4: Production of Grafted Antimicrobial Polyvinyl Chloride Masterbatch The procedure of Example 3 may be followed in the presence of about 0.05 wt % peroxide. The presence of the peroxide will result in a grafting of the antimicrobial ingredient onto the polymer to produce a grafted antimicrobial plasticized PVC master batch.

Example 5: Production of an Alternative Antimicrobial Polyvinyl Chloride

An alternative antimicrobial polyvinyl chloride may be produced using the procedure of Example 3 but substituting chlorhexidine digluconate as plasticizer antimicrobial active ingredient.

Example 6: Preparation of Polypropylene Grafted Antimicrobial by Direct Grafting A polypropylene having antimicrobial properties may be produced by mixing about 1 wt % of antimicrobial ingredient cetyltrimethylammonium bromide with polypropylene in the presence of about 0.05 wt % peroxide. The mixture may be fed into a reactive extruder and injection molded to form toys.

Example 7: Copolymerizing Reactive Quaternary Ammonium Salt with Vinylacetate Using Free Radical Polymerization A polymer having antimicrobial properties may be produced by copolymerizing 1-heptadecenyltrimethylammonium bromide ($CH_2=CH(CH_2)_{15}N$ $(CH_3)_3$ Br) with vinyl acetate co-monomer by free radical polymerization. A standard bulk polymerization may be done using vinyl acetate as a primary co-monomer and reactive 1-heptadecenyltrimethylammonium bromide in wt. ratio of about 90:5 in the presence of about 0.5 wt % benzoyl peroxide as free radical initiator under an inert $N_2$ atmosphere. The antimicrobial polymer may be cast to antimicrobial polyvinylacetate films and used in food packaging.

Example 8: Production of Antimicrobial Polycarbonate by Chain-End Termination An antimicrobial polycarbonate may be produced by condensation of about 0.1 mole of bisphenol A, and phosgene using standard heterogeneous or mixed homogenous polymerization. After a predetermined reaction time, about 0.1 mole of 1-hydroxycetyl-trimethylammonium bromide may be added to terminate the polymerization by blocking the chain ends with antimicrobial active ingredient. The 1-hydroxycetyltrimethylammonium bromide may also react with any traces of unreacted bisphenol-A to advantageously remove unreacted bisphenol-A from the resin. The obtained antimicrobial polycarbonate may be processed into final products by any of the common technological methods as discussed previously.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, that form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for making an antimicrobial masterbatch, the method comprising: mixing an antimicrobial ingredient with a polymer comprising a melt flow index of about 10 g/10 minutes to about 50 g/10 minutes, as measured in accordance with ASTM D-1238 at 190 ° C. and 2.16 kg load, and a catalyst at a temperature, shear, and pressure sufficient to graft the antimicrobial ingredient to the polymer to form the antimicrobial masterbatch, wherein mixing the antimicrobial ingredient comprises mixing at least one of the following: a quaternary phosphonium salt, chlorhexidine, polyhexamethylene biguanide, povidone iodine, starch-iodine, and their derivatives with any of the following: a butyrate, a gluconate, an octanoate, an adipate, a sebacate, a caproate, an aliphatic diester, a low molecular weight aliphatic polyester, a low molecular weight polyether, a low molecular weight polyamide, and combinations thereof.

2. The method of claim 1, wherein:
the mixing comprises mixing the antimicrobial ingredient, the polymer, and the catalyst in a reactive extruder at the temperature, shear, and pressure sufficient to graft the antimicrobial ingredient to the polymer; and the method further comprises extruding the antimicrobial masterbatch from the reactive extruder.

3. The method of claim 2, wherein the extruding comprises forming pellets of the antimicrobial masterbatch.

4. The method of claim 1, wherein mixing the catalyst comprises mixing a peroxide catalyst comprising at least one peroxide group.

5. The method of claim 4, wherein the peroxide catalyst comprises at least one of the following: benzoyl peroxide; cumyl peroxide; dicumyl peroxide; cumyl hydroperoxide; t-butyl-cumyl peroxide; 1,3-bis(t-butylperoxyisopropyl) benzene; t-butyl hydroperoxide; di-t-butyl peroxide; 2,5-dimethyl-2,5-di(t-butylperoxy)hexane; t-butyl-perbenzoate; 1,1,3,3-tetramethylbutyl hydroperoxide; 2,5-dimethylhexyl 2,5-diperoxy-benzoate; 2,5-dimethylhexane 2,5-dihydroperoxide; and 2,5-dimethyl 2,5-bis(t-butylperoxy)hexene-3.

6. The method of claim 1, wherein mixing the antimicrobial ingredient with the polymer comprises mixing with at least one polyolefin.

7. The method of claim 1, wherein the polymer comprises at least one of the following: polyethylene, polypropylene, polymethylpentene, polybutene-1, an ethylene-vinyl acetate copolymer, polystyrene, polyethylene terephthalate, polyvinyl acetate, polycarbonate, polyamide, polyvinyl alcohol, polyvinylidene chloride, an acrylonitrile butadiene styrene copolymer, an acrylic polymer, an acrylic copolymer, a polysulfone, a polyvinyl chloride polymer, a polyvinyl chloride copolymer, butyl rubber, isoprene rubber, a silicone thermoplastic, and a silicon rubber.

8. The method of claim 1, wherein the antimicrobial ingredient in the antimicrobial masterbatch is in an amount of about 20 wt % to about 50 wt % of an amount of the polymer.

9. The method of claim 4, wherein mixing the catalyst comprises mixing an amount of the peroxide catalyst from about 0.025 wt % to about 0.05 wt % of an amount of the polymer.

10. The method of claim 4, wherein mixing the catalyst comprises mixing at the temperature sufficient for decomposing the peroxide catalyst, and for melt processing of the polymer.

11. A method for making an antimicrobial polymer, the method comprising: mixing a polymer with a dual acting ingredient comprising an antimicrobial ingredient covalently bonded to a plasticizer at a temperature, shear, and pressure sufficient to distribute the dual acting ingredient into the polymer to form the antimicrobial polymer.

12. The method of claim 11, wherein forming the antimicrobial polymer comprises forming an antimicrobial masterbatch having a weight ratio of the polymer to the dual acting ingredient from about 1:20 to about 1:50.

13. The method of claim 11, wherein the mixing comprises mixing a weight ratio of the polymer to the dual acting ingredient from about 100:1 to about 100:2.

14. The method of claim 11, wherein mixing the antimicrobial ingredient comprises mixing at least one of the following: a quaternary ammonium salt, a quaternary phosphonium salt, chlorhexidine, polyhexamethylene biguanide, povidone iodine, starch-iodine and their derivatives with any of the following: a butyrate, a gluconate, an octanoate, an adipate, a sebacate, a caproate, an aliphatic diester, a low molecular weight aliphatic polyester, a low molecular weight polyether, and a low molecular weight polyamide.

15. The method of claim 11, wherein the plasticizer is at least one of the following: an adipate, a sebacate, a caproate, an aliphatic diester, a low molecular weight aliphatic polyester, a low molecular weight polyether, and a low molecular weight polyamide.

16. The method of claim 11, wherein mixing the dual-acting ingredient comprises mixing at least one of the following: chlorhexidine butyrate, chlorhexidine octanoate, chlorhexidine caproate, chlorhexidine digluconate, biguanide grafted to a low molecular weight polymeric plasticizer, cetyltrimethylammonium bromide grafted to a low molecular weight polymeric plasticizer, and derivatives of the antimicrobial ingredient with any of the following: an adipate, a sebacate, a caproate, an aliphatic diester, a low molecular weight aliphatic polyester, a low molecular weight polyether, and a low molecular weight polyamide.

17. The method of claim 11, wherein:
the mixing comprises mixing the dual acting ingredient and the polymer in a reactive extruder in the presence of a peroxide catalyst to form the antimicrobial polymer; and
the method further comprises extruding the antimicrobial polymer from the reactive extruder.

18. A method for producing an antimicrobial polymer, the method comprising copolymerizing a reaction mixture comprising:
a first polymerizable co-monomer comprising a dual acting antimicrobial-plasticizer having an antimicrobial ingredient covalently bonded to a plasticizer; and
a second polymerizable co-monomer.

19. The method of claim 18, wherein copolymerizing the second polymerizable co-monomer comprises reacting at least one member selected from the group comprising: ethylene, propylene, vinylacetate, acrylate, diols, diamines, diacids, diesters, diisocyanates, diepoxides, caprolactam, caprolactone, olefenic co-monomer, a condensation comonomer, and a cyclic monomer.

20. The method of claim 18, wherein:
the antimicrobial ingredient is at least one of the following: a quaternary ammonium salt, a quaternary phosphonium salt, chlorhexidine, polyhexamethylene biguanide, povidone iodine, starch-iodine, and their derivatives with any of the following: a butyrate, a gluconate, an octanoate, an adipate, a sebacate, a caproate, an aliphatic diester, a low molecular weight aliphatic polyester, a low molecular weight polyether, and a low molecular weight polyamide.

21. The method of claim 18, wherein
the dual acting antimicrobial-plasticizer having the antimicrobial ingredient is at least one of the following: chlorhexidine butyrate, chlorhexidine octanoate, chlorhexidine caproate, chlorhexidine digluconate, biguanide grafted to a low molecular weight polymeric plasticizer, and cetyltrimethylammonium bromide grafted to a low molecular weight polymeric plasticizer.

22. A method for producing antimicrobial polymer products, the method comprising:
charging a reactive extruder with a high melt flow rate polymer, a catalyst, and an antimicrobial ingredient, wherein the antimicrobial ingredient comprises at least one of the following: a quaternary phosphonium salt, a chlorhexidine, a polyhexamethylene biguanide, povidone iodine, starch-iodine, and their derivatives with any of the following: a butyrate, a gluconate, an octanoate, an adipate, a sebacate, a caproate, an aliphatic diester, a low molecular weight aliphatic polyester, a low molecular weight polyether, a low molecular weight polyamide, and combinations thereof;

operating the reactive extruder at a temperature, shear, and pressure sufficient to graft the antimicrobial ingredient to the high melt flow rate polymer to form an antimicrobial masterbatch;

extruding the antimicrobial masterbatch;

mixing the antimicrobial masterbatch with a melt-processable polymer;

applying heat, shear, and pressure to disperse the antimicrobial ingredient of the antimicrobial masterbatch into the melt-processable polymer to produce an antimicrobial polymer; and processing the antimicrobial polymer into the antimicrobial polymer products capable of inhibiting growth of microorganisms in or on the antimicrobial polymer products.

23. The method of claim 22, wherein the processing comprises at least one of the following: vacuum forming, blow molding, injection molding, extrusion, rotational molding, injection blow molding, compression molding, solution casting, emulsion, and spraying.

24. The method of claim 22, wherein charging the reactive extruder comprises charging the reactive extruder with the catalyst comprising at least one peroxide group.

25. The method of claim 24, wherein operating the reactive extruder comprises operating the reactive extruder at a temperature sufficient for decomposing the at least one peroxide group, and melt processing the high melt flow rate polymer.

26. The method of claim 22, wherein forming the antimicrobial masterbatch comprises forming a masterbatch comprising an amount of the antimicrobial ingredient in the antimicrobial masterbatch from about 20 wt % to about 50 wt % of an amount of the high melt flow rate polymer.

27. The method of claim 22, wherein producing the antimicrobial polymer comprises producing a polymer comprising an amount of the antimicrobial ingredient from about 0.25 wt % to about 2 wt % of an amount of the melt-processable polymer.

28. The method of claim 22, wherein each of the high melt flow rate polymer and the melt-processable polymer comprises at least one of the following: polyethylene, polypropylene, polymethylpentene, polybutene-1, an ethylene-vinyl acetate copolymer, polystyrene, polyethylene terephthalate, polyvinyl acetate, polycarbonate, polyamide, polyvinyl alcohol, polyvinylidene chloride; an acrylonitrile butadiene styrene copolymer, an acrylic polymer, an acrylic copolymer, a polysulfone, a polyvinyl chloride polymer, a polyvinyl chloride copolymer, butyl rubber, isoprene rubber, and a silicone thermoplastic.

29. The method of claim 1, wherein the grafting the antimicrobial ingredient comprises grafting the antimicrobial ingredient on the polymer at one or more of terminal ends of the polymer and backbone of the polymer.

30. The method of claim 1, wherein the antimicrobial ingredient in the antimicrobial masterbatch is in an amount of about 40 wt % to about 50 wt % of an amount of the polymer.

* * * * *